(12) United States Patent
Hibi

(10) Patent No.: US 8,243,128 B2
(45) Date of Patent: Aug. 14, 2012

(54) ELECTRONIC ENDOSCOPE

(75) Inventor: Haruhiko Hibi, Tokyo (JP)

(73) Assignee: Hoya Corporation, Tokyo (JP)

( * ) Notice: Subject to any disclaimer, the term of this patent is extended or adjusted under 35 U.S.C. 154(b) by 1532 days.

(21) Appl. No.: 11/537,052

(22) Filed: Sep. 29, 2006

(65) Prior Publication Data

US 2007/0076091 A1   Apr. 5, 2007

(30) Foreign Application Priority Data

Sep. 30, 2005   (JP) ................................ P2005-286243

(51) Int. Cl.
*A62B 1/04* (2006.01)
*A61B 1/04* (2006.01)
*G03F 3/08* (2006.01)

(52) U.S. Cl. ............... 348/65; 348/71; 396/17; 358/518
(58) Field of Classification Search ................ None
See application file for complete search history.

(56) References Cited

U.S. PATENT DOCUMENTS

| 5,216,496 | A  | * | 6/1993  | Miyamoto et al. ............ 348/237 |
| 6,154,248 | A  |   | 11/2000 | Ozawa et al. |
| 6,319,198 | B1 |   | 11/2001 | Takahashi |
| 6,466,256 | B1 |   | 10/2002 | Takahashi et al. |
| 6,635,011 | B1 |   | 10/2003 | Ozawa et al. |
| 6,943,822 | B2 |   | 9/2005  | Iida et al. |
| 6,980,227 | B2 |   | 12/2005 | Iida et al. |
| 2003/0001952 | A1 |   | 1/2003 | Iida et al. |
| 2003/0071895 | A1 | * | 4/2003 | Higuchi et al. ................. 348/65 |
| 2003/0076411 | A1 |   | 4/2003 | Iida et al. |
| 2005/0046695 | A1 | * | 3/2005 | Takasugi ........................ 348/71 |
| 2005/0243169 | A1 | * | 11/2005 | Ono et al. ....................... 348/65 |

FOREIGN PATENT DOCUMENTS

| JP | 58-170183 | 10/1983 |
| JP | 10-75441  | 3/1998 |
| JP | 11-027695 | 1/1999 |

OTHER PUBLICATIONS

Wolf, Stephen, "Color Correction Matrix for Digital Still and Video Imaging Systems", NTIA Technical Memorandum TM-04-406, Dec. 2003.*
Japan Office action, dated Aug. 23, 2011 along with an english translation thereof.

* cited by examiner

*Primary Examiner* — Joseph Ustaris
*Assistant Examiner* — Frederick Bailey
(74) *Attorney, Agent, or Firm* — Greenblum & Bernstein, P.L.C.

(57) ABSTRACT

An electronic endoscope has a video-scope with an image sensor, and a signal processor that generates digital component video signals from image-pixel signals that are read from the image sensor. The electronic endoscope has, further, a color-reverse detector that determines whether a color-reverse occurs in the digital component video signals, and a color correcting processor that changes color signal data associated with the color-reverse so as to correct the color-reverse when the color-reverse occurs.

7 Claims, 5 Drawing Sheets

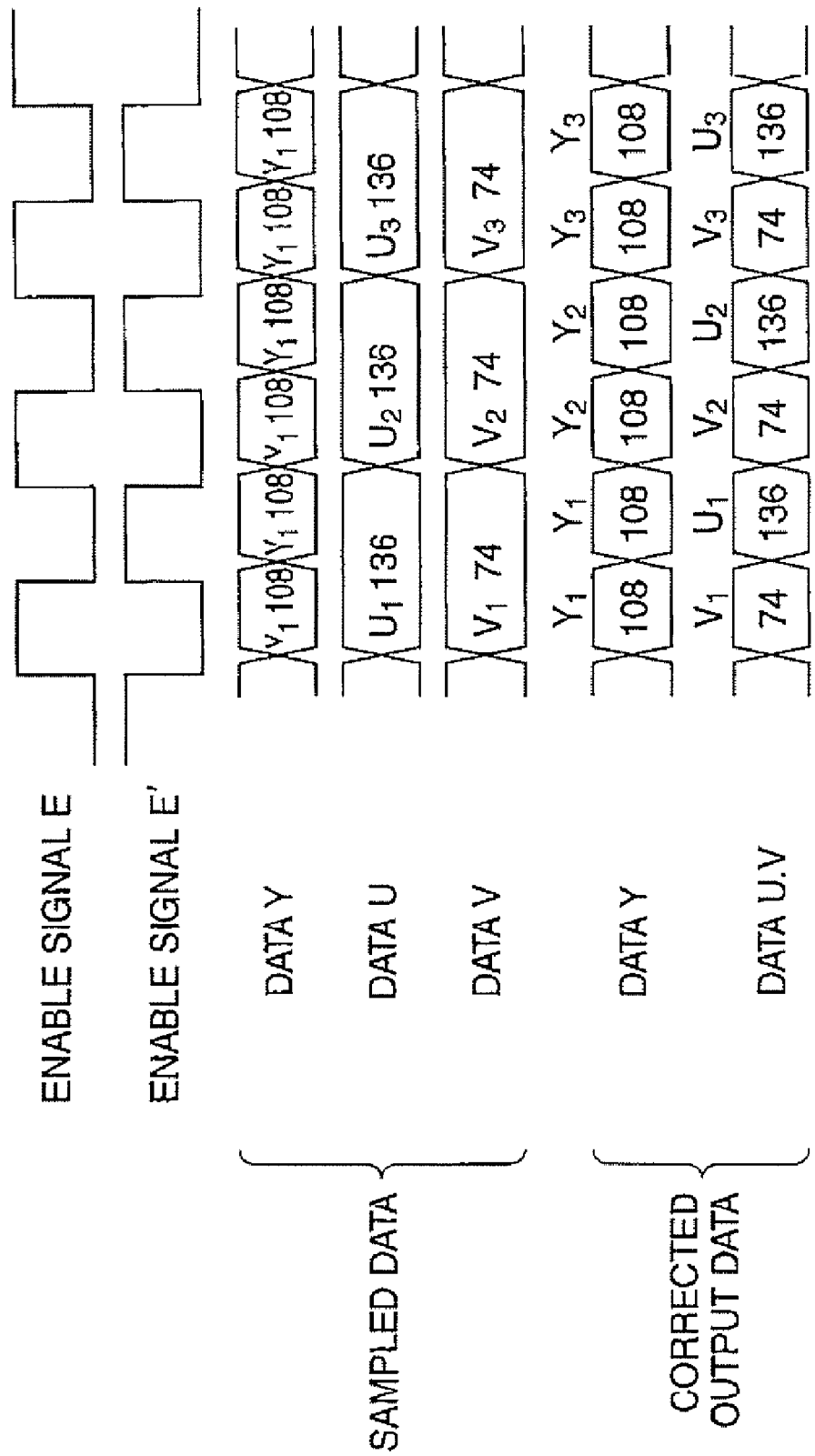

ELECTRONIC ENDOSCOPE

BACKGROUND OF THE INVENTION

1. Field of the Invention

The present invention relates to an electronic endoscope having a video-scope. In particular, it relates to a signal process for displaying a color image.

2. Description of the Related Art

In an electronic endoscope, a video-scope with an image sensor is inserted into a body cavity such as a stomach, and image-pixel signals corresponding to an observed image are read from the image sensor. In a video-processor, video signals are generated on the basis of the image-pixel signals and are output to a monitor, so that an observed image is displayed on the monitor. As for video signals, in addition to analog image signals, digital image signals are generated. For example, digital component video signals composed of luminance signals (Y) and color difference signals (U, V) are generated from primary color (R, G, B) digital video signals. A signal process for generating the video signals is performed while synchronizing clock pulse signals, which are output from a clock pulse generator.

A phase of the clock pulse signals is occasionally reversed; in other words, a high level and a low level of the clock pulse signals are switched, due to characteristics of the power supplying circuit or of a connection of the video-scope. When the phase of the clock pulse signals is reversed, a phase of the generated digital component video signals is also reversed, so that an observed image in which color is reversed is displayed on the monitor. For example, a reddish observed image becomes a bluish observed image.

SUMMARY OF THE INVENTION

An object of the present invention is to provide an apparatus that is capable of displaying a color image faithfully regardless of a phase reverse of clock pulse signals.

An electronic endoscope according to the present invention has a video-scope with an image sensor, and a signal processor that generates digital component video signals from image-pixel signals that are read from the image sensor. The electronic endoscope has, further, a color-reverse detector that determines whether a color-reverse occurs in the digital component video signals, and a color correcting processor that changes color signal data associated with the color-reverse so as to correct the color-reverse when the color-reverse occurs.

BRIEF DESCRIPTION OF THE DRAWINGS

The present invention will be better understood from the description of the preferred embodiments of the invention set forth below together with the accompanying drawings, in which:

FIG. 5 is a view showing a part of the data array of the digital component video signals shown in FIG. 4.

DESCRIPTION OF THE PREFERRED EMBODIMENTS

Hereinafter, the preferred embodiment of the present invention is described with reference to the attached drawings.

Figure 1:
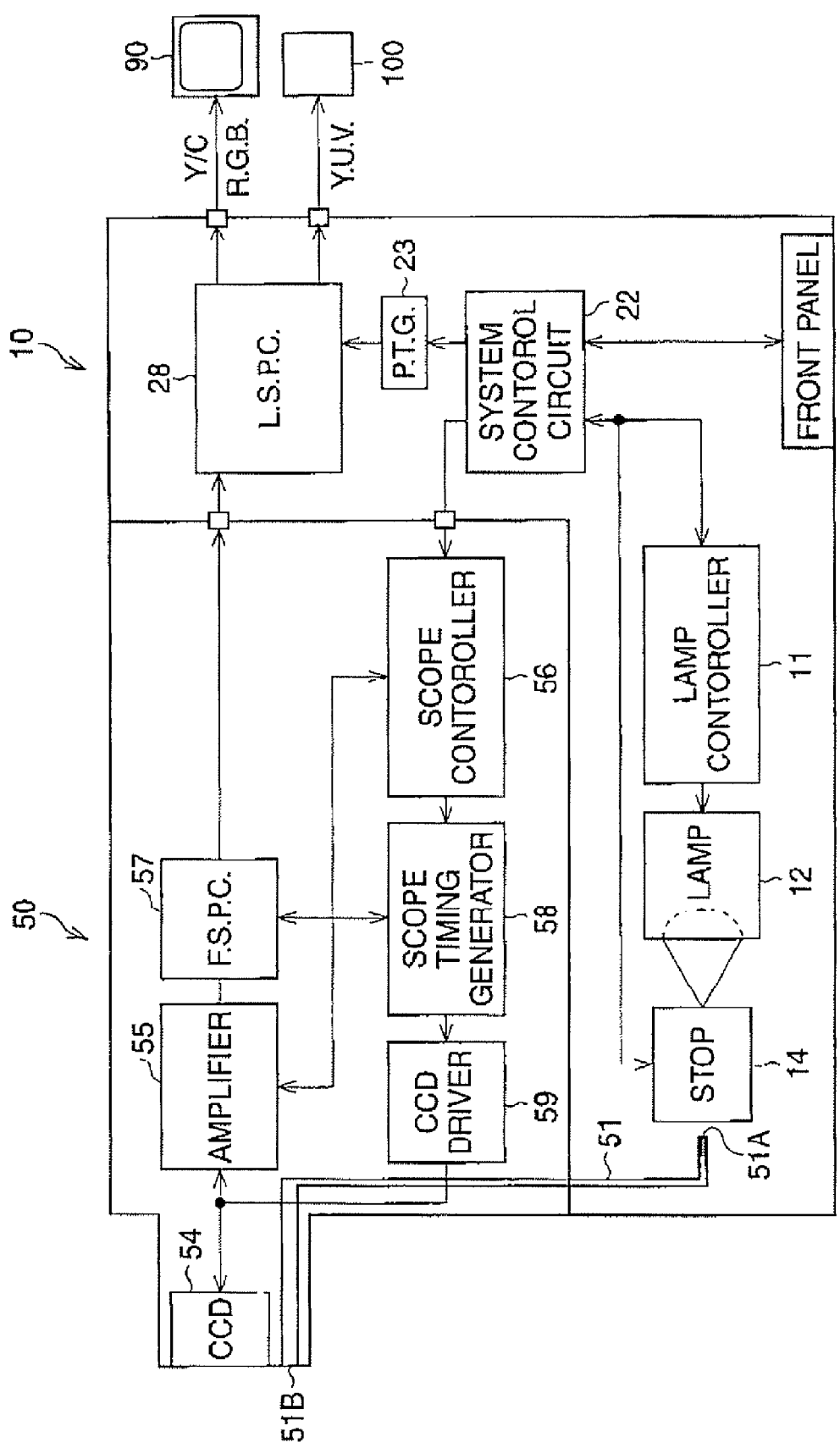
FIG. 1 is a block diagram of an electronic endoscope according to the present embodiment.

FIG. 1 is a block diagram of an electronic endoscope according to the present embodiment.

An electronic endoscope is equipped with a video-scope 50 having a CCD 54 and a video-processor 10, which is connected to the video-scope 50. A computer 100 and a monitor 90 are connected to the video-processor 10.

When a lamp switch (not shown) is turned ON, electric power is supplied from a lamp controller 11 to a lamp 12, so that the lamp 12 is turned ON. Light emitted from the lamp 12 passes a collecting lens (not shown) and a stop 14, and enters into an incident surface 51A of a light guide 51. The light guide 51, composed of a fiber-optic bundle, directs the light to the tip portion of the video-scope 50. The light passing through exits from the end surface 51B of the light guide 51, and exits from the video-scope 50 via a diffusion lens (not shown), so that an observed portion is illuminated.

Light reflected off the observed portion passes an objective lens (not shown) and reaches the CCD 54, so that an object image is formed on a photo-sensor area of the CCD 54. As for the imaging method, an on-chip color filter method using an on-chip color filter is herein applied. On the photo-sensor area of the CCD 54, a complementary color filter (not shown), checkered by four color elements, Yellow (Y), Magenta (Mg), Cyan (Cy), and Green (G), is arranged such that each area of the four color elements is opposite a pixel.

In the COD 54, image-pixel signals, corresponding to light passing through the complementary color filter, are generated by the photoelectric effect. A CCD driver 59 outputs clock pulse signals to the CCD 54, so that the analog image-pixel signals are read from the CCD 54 at regular time intervals in accordance with a so-called "color difference line sequential system". Herein, the NTSC or PAL standard is applied; thus, one field-worth of image-pixel signals are successively read from the CCD 13 at 1/60- or 1/50-second time intervals. The image-pixel signals are then fed to a first signal processing circuit 57 via an amplifier 55. In the first signal processing circuit 57, a given process is performed on the image-pixel signals, and processed analog image signals are fed from the first signal processing circuit 57 to a latter signal processing circuit 28 provided in the video processor 10.

In the latter signal processing circuit 28, various processes, such as a white balance process, a gamma correction process, and an A/D conversion process, are performed on the image signals, so that R, G, and B analog video signals and primary color (R, G, B) digital video signals are generated. The analog video signals are directly output to the monitor 90 as video signals. On the other hand, in the latter signal processing circuit 28, the R, G, and B digital video signals are converted to luminance (Y) and color difference (U, V) digital component video signals, which are fed to a computer system 100. In the computer system 100, an observed image is displayed on a computer monitor, or is recorded on a recorder.

A system control circuit 22, including a CPU (not shown), controls the video-processor 10, and outputs control signals to each circuit. A processor timing generator 23 outputs clock pulse signals to adjust a timing of a signal process for each circuit in the video-processor 10. A scope controller 56 controls the video-scope 50, and outputs control signals to the first signal processing circuit 57 and to a scope timing generator 58. When the video-scope 50 is connected to the video-processor 10, data is transmitted between the scope controller 56 and the system control circuit 22.

Figure 2:
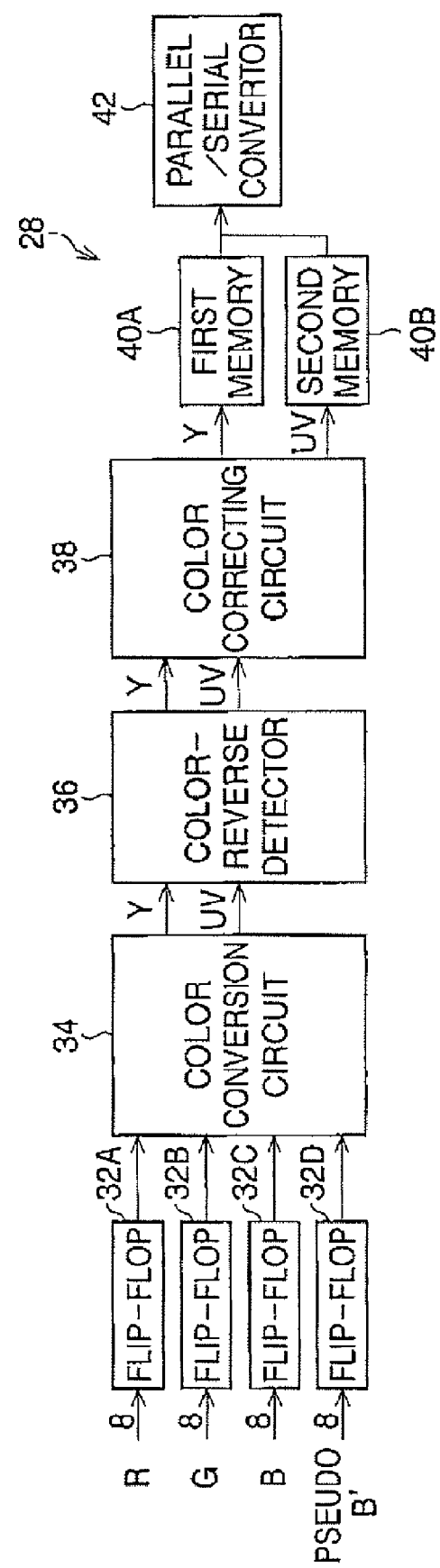
FIG. 2 is a block diagram of the latter signal processing circuit.
Figure 3:
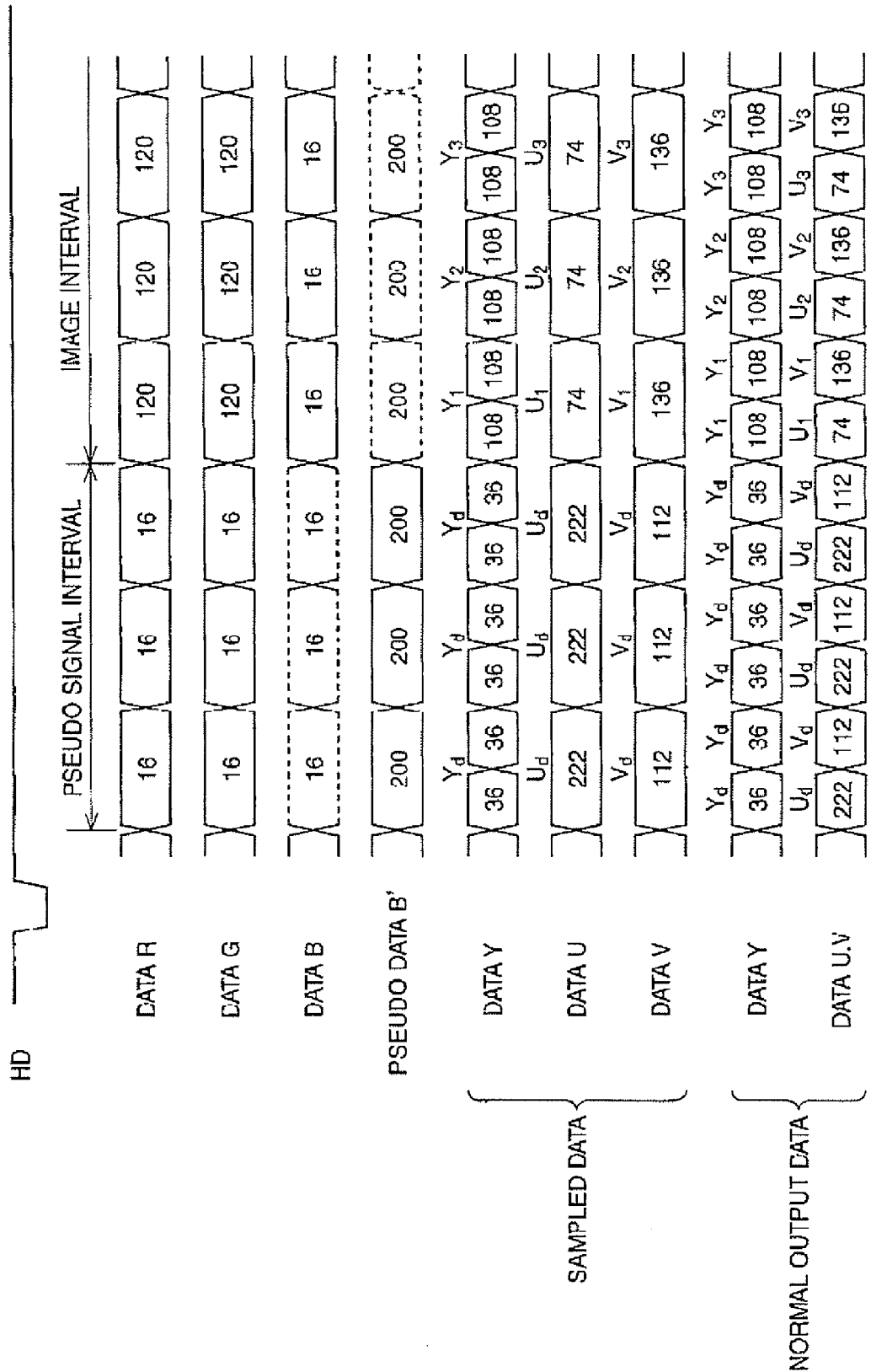
FIG. 3 is a view showing a normal data array of the digital component video signals.
Figure 4:
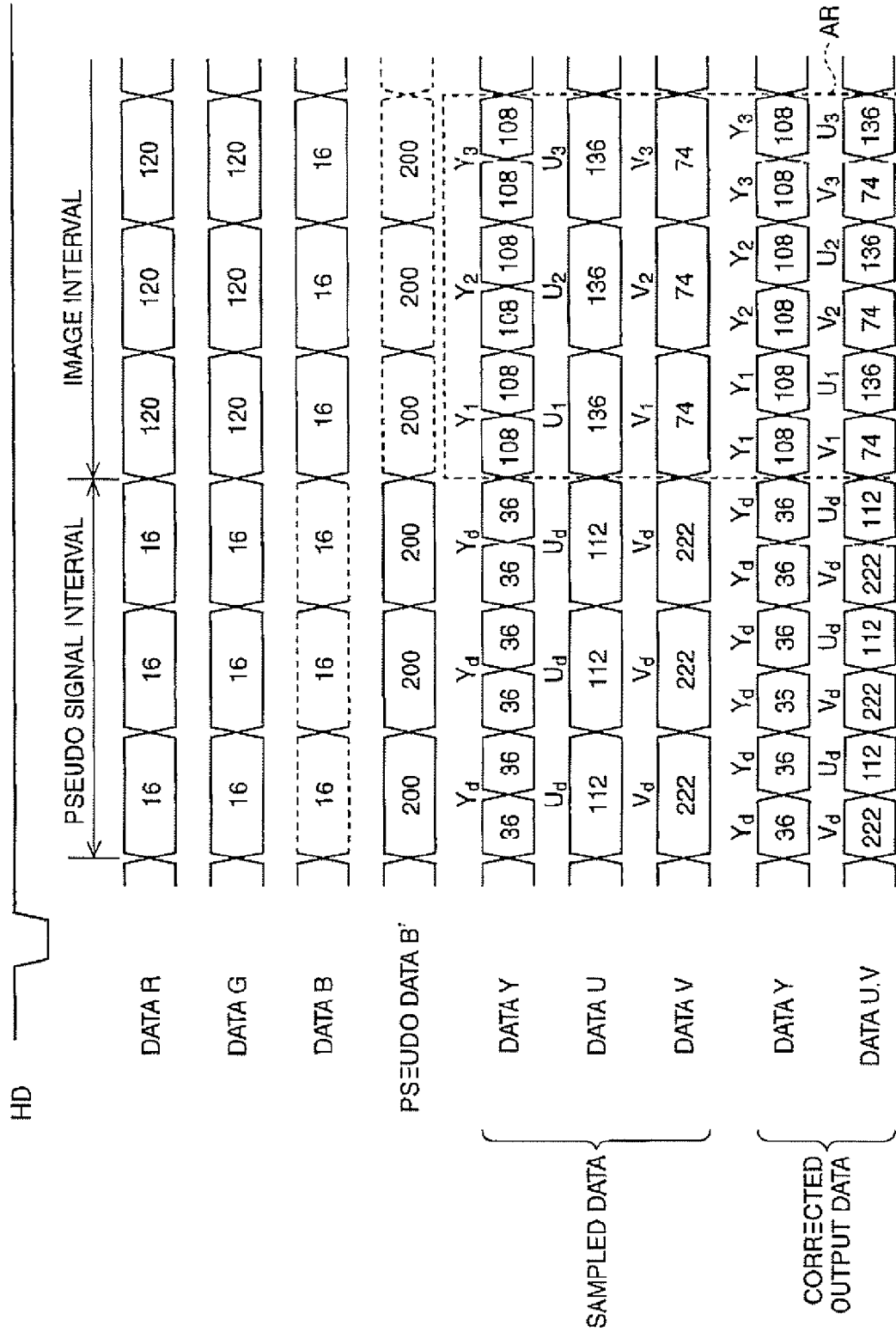
FIG. 4 is a view showing a corrected data array of the digital component video signals.

FIG. 2 is a block diagram of the latter signal processing circuit 28. FIG. 3 is a view showing a normal data array of the digital component video signals. FIG. 4 is a view showing a corrected data array of the digital component video signals. FIG. 5 is a view showing a part of the data array of the digital component video signals shown in FIG. 4. Note that, in FIG. 2, only components associated with a color correcting process are shown.

The generated R, G, and B digital video signals are composed of 8-bit data, and are input to a flip-flop 32A, a flip-flop 32B, and a flip-flop 32C, respectively. The value of each color component signals is in a range between 0 and 255. R, G, and B color signals are output from the flip-flops 32A, 32B, and 32C to a color conversion circuit 34 while synchronizing one another. In addition to the R, G, and B digital video signals, other blue color signals "B'" for detecting the color-reverse (hereinafter, called "pseudo blue signals") are input to the color conversion circuit 34 via a flip-flop 32D while synchronizing the R, G, and B digital video signals. The pseudo blue signals B' are input at an initial interval corresponding to a blank interval (hereinafter, called a "pseudo signal interval") in a one-line image interval; namely, at the head position of a series of R, G, and B color component data corresponding to one line-worth of R, C, B video signals (see FIG. 3). In the color conversion circuit 34, the R, G, and B digital video signals are converted to luminance "Y" and color difference "U, V" digital component video signals by a matrix operation. The matrix operation is performed in accordance with horizontal synchronizing signals HD, which depend upon the display-characteristics of the monitor 90.

In the pseudo signal interval, the luminance Y and color difference U, V digital component video signals are generated on the basis of the pseudo blue signals B', instead of the actual blue color component signals B. The value of each of the pseudo blue signals B' is predetermined to be a relatively high value compared to the value or the R and G color component signals, which are prepared for the pseudo signal interval, so that the value of color difference data "$U_d$" becomes a relatively high value (see FIG. 3), and Y, U, and V digital component video signals that includes many blue color components are generated. Herein, the value of each of the pseudo blue signals B' is set to 200, whereas the value of each of R and G color component signals is set to 16 (see FIG. 3). In an interval after the pseudo interval (herein, called an "image interval"), the luminance Y and color difference U, V digital component video signals are generated on the basis of the R, G, and B digital video signals obtained from the image-pixel signals.

Further, in the color conversion circuit 34, the luminance Y and color difference U, V digital component video signals are subjected to a sampling process using predetermined sampling frequencies. The ratio of the sampling frequencies of Y, U, and V to one another is determined on the basis of the digital video standard. Herein, the ratio of sampling frequencies Y, U, and V is set to 4:2:2. The generated luminance Y and color difference U, V digital component signals are fed to a color-reverse detector 36.

In the color-reverse detector 36, it is determined whether the color difference data $U_d$, $V_d$ obtained from the pseudo blue signals B' have been replaced. When the phase of the clock pulse signals, which are output from the processor timing generator 23, are shifted relative to the horizontal synchronizing signals HD (namely, when an ON-OFF timing of the clock pulse signals is reversed), the color-reverse occurs, in which case the color difference data $U_d$ corresponding to blue color components and the color difference data $V_d$ corresponding to red color components are switched. Consequently, the value of the color difference data $U_d$ becomes low. In FIG. 4, the values of the color difference data $U_d$, $V_d$ have been replaced to 112, 222. The color-reverse detector 36 detects the value of the color difference data $U_d$ and determines whether the value of the color difference data $U_d$ is lower than a predetermined value. Herein, the predetermined value is set to a value in the range of 160 to 200.

When it is determined that color-reverse has not occurred, the luminance data Y and the color difference data U, V are directly input to and output from a color correcting circuit 38. Then, the luminance data Y are fed to a first memory 40A, and the color difference data U, V are fed to a second memory 40B. Thus, luminance and color difference digital component signals (Y, U, V) in which the data are arrayed as "$Y_1, U_1, Y_1, V_1, Y_2, U_2, Y_2, V_2, \ldots$" are generated (See FIG. 3). The luminance and the color difference component digital signals are converted from parallel data to serial data in a parallel/serial converter 42.

On the other hand, when it is determined that the color-reverse has occurred, in the color correcting circuit 38, a color correcting process is performed on the luminance and color difference digital component video signals. Namely, the order of data in the data array is replaced or substituted with respect to the color difference data U, V. The luminance data Y are fed to the first memory 40A, and the order-replaced color luminance data V, U are fed to the second memory 40B. Thus, luminance Y and color difference U, V digital component signals in which the data are arrayed as "$Y_1, V_1, Y_1, U^1, Y_2, V_2, Y_2, U_2, \ldots$" are generated (see FIGS. 4 and 5). The corrected digital component signals are output from the color correcting circuit 38 as luminance and color difference digital component video signals (Y, U, V).

In this way, in the present embodiment, the color-reverse detector 36 determines whether the color-reverse occurs in the luminance and color difference digital component signals, by using the pseudo blue signals B'. When the color-reverse occurs, the data array of the color difference data U and V are switched. Thus, a construction of a timing generator becomes a simple construction since an exclusive synchronization adjustment circuit is not needed.

Optionally, the color-reverse may be detected without a color-reverse detector. For example, an enablement signal E synchronizing with the horizontal synchronizing signal HD is converted to a phase-shifted enablement signal E' when the color-reverse occurs (see FIG. 4). The color difference data U is selected when the enablement signal E is at a high level, whereas the color difference data V is selected when the enablement signal E is at a low level.

To detect the color-revise, the color-reverse detector may detect whether the value of the one color difference data $U_d$ is 222. Further, the R signals may be set to pseudo signals, and $V_d$ signals may be used to detect the color-revise.

The signal process for generaLing digital component video signals and the color correcting process may be performed in the video-scope.

Finally, it will be understood by those skilled in the arts that the foregoing description is of preferred embodiments of the device, and that various changes and modifications may be made to the present invention without departing from the spirit and scope thereof.

The present disclosure relates to subject matter contained in Japanese Patent Application No. 2005-286243 (filed on Sep. 30, 2005), which is expressly incorporated herein, by reference, in its entirety

The invention claimed is:

1. An electronic endoscope, comprising:
a video-scope with an image sensor;
a signal processor that generates digital component video signals from image-pixel signals that are read from said image sensor;
a color-reverse detector that determines whether a color-reverse occurs in the digital component video signals; and
a color correcting processor that changes color signal data associated with the color-reverse so as to correct the color-reverse when the color-reverse occurs, wherein
said signal processor converts red-, green-, and blue-color digital video signals obtained from the image-pixel signals to luminance and color difference digital component video signals, said color-reverse detector determining whether color difference data in the luminance and color difference digital component video signals are switched, said color correcting processor replacing the order of data in the data array in the color difference data,
said color-reverse detector inputs a pseudo signal for detecting the color-reverse to said signal processor, said color-reverse detector determining whether color difference data obtained from the pseudo signal are switched, and
said color-reverse detector interleaves the pseudo signal at a head position of one line-worth of red, green, and blue digital video signals, said color correcting processor replacing the color difference data that follow the pseudo signal.

2. The electronic endoscope of claim 1, wherein the color-reverse detector detects whether the array of the color signal data is replaced.

3. The electronic endoscope of claim 1, wherein said color said color-reverse detector determining whether a color of digital component video signals obtained from the pseudo signal is reversed.

4. The electronic endo scope of claim 3, wherein the pseudo signal has specific color components, said color-reverse detector determining whether the specific color components are exhibited in the digital video component signals.

5. The electronic endo scope of claim 1, wherein the pseudo signal has relatively more red or blue color components compared to the other color components, said color-reverse detector determining whether one of the color difference signal corresponding to the blue color components and color difference signal corresponding to the red color components has a relatively high value.

6. A video-processor connected to a video-scope with an image sensor, comprising:
a signal processor that generates digital component video signals from image-pixel signals that are read from said image sensor;
a color-reverse detector that determines whether a color-reverse occurs in color signal data included in the digital component video signals; and
a color correcting processor replaces an order of an array of the color signal data so as to correct the color-reverse when it is determined that the color-reverse occurs, wherein said signal processor converts red-, green-, and blue-color digital video signals obtained from the image-pixel signals to luminance and color difference digital component video signals, said color-reverse detector determining whether color difference data in the luminance and color difference digital component video signals are switched, said color correcting processor replacing the order of data in the data array in the color difference data,
said color-reverse detector inputs a pseudo signal for detecting the color-reverse to said signal processor, said color-reverse detector determining whether color difference data obtained from the pseudo signal are switched, and
said color-reverse detector interleaves the pseudo signal at a head position of one line-worth of red, green, and blue digital video signals, said color correcting processor replacing the color difference data that follow the pseudo signal.

7. An apparatus for correcting color, comprising:
a signal processor that generates digital component video signals from image-pixel signals that are read from an image sensor, said image sensor is provided in a video-scope;
a color-reverse detector that determines whether a color-reverse occurs in color signal data included in the digital component video signals; and
a color correcting processor replaces an order of an array of the color signal data so as to correct the color-reverse when it is determined the color-reverse occurs, wherein said signal processor converts red-, green-, and blue-color digital video signals obtained from the image-pixel signals to luminance and color difference digital component video signals, said color-reverse detector determining whether color difference data in the luminance and color difference digital component video signals are switched, said color correcting processor replacing the order of data in the data array in the color difference data
said color-reverse detector inputs a pseudo signal for detecting the color-reverse to said signal processor, said color-reverse detector determining whether color difference data obtained from the pseudo signal are switched, and
said color-reverse detector interleaves the pseudo signal at a head position of one line-worth of red, green, and blue digital video signals, said color correcting processor replacing the color difference data that follow the pseudo signal.

* * * * *